United States Patent
Park et al.

(10) Patent No.: US 9,138,303 B2
(45) Date of Patent: Sep. 22, 2015

(54) ROTARY TOOTHBRUSH

(71) Applicant: HINT CO., LTD., Gyeonggi-do (KR)

(72) Inventors: Jong Chan Park, Chungcheongbuk-do (KR); Man Joong Kim, Daejeon (KR); Jung Wan Woo, Daejeon (KR); Jung Tak Woo, Daejeon (KR)

(73) Assignee: HINT CO., LTD. (KR)

( * ) Notice: Subject to any disclaimer, the term of this patent is extended or adjusted under 35 U.S.C. 154(b) by 172 days.

(21) Appl. No.: 13/934,444

(22) Filed: Jul. 3, 2013

(65) Prior Publication Data

US 2014/0020195 A1  Jan. 23, 2014

(30) Foreign Application Priority Data

Jul. 17, 2012 (KR) .................. 10-2012-0077935
May 30, 2013 (KR) .................. 10-2013-0061549

(51) Int. Cl.
- A61C 17/24 (2006.01)
- A46B 5/00 (2006.01)
- A46B 7/02 (2006.01)

(52) U.S. Cl.
CPC ............... *A61C 17/24* (2013.01); *A46B 5/0083* (2013.01); *A46B 7/02* (2013.01); *A46B 5/0095* (2013.01); *A46B 2200/1066* (2013.01)

(58) Field of Classification Search
CPC ...... A46B 9/04; A46B 5/0075; A46B 5/0083; A46B 2200/1066
USPC ................................. 15/167.1, 172
See application file for complete search history.

(56) References Cited

U.S. PATENT DOCUMENTS

| 4,333,199 | A | * | 6/1982 | Del Rosario | 15/167.1 |
| 5,867,856 | A | | 2/1999 | Herzog | |
| 5,884,354 | A | * | 3/1999 | Anderson | 15/167.1 |
| 2005/0144744 | A1 | | 7/2005 | Thiess et al. | |
| 2006/0254007 | A1 | | 11/2006 | Banning | |
| 2008/0172812 | A1 | | 7/2008 | Dean | |
| 2013/0000061 | A1 | | 1/2013 | Park et al. | |

FOREIGN PATENT DOCUMENTS

| JP | 63-153833 U | 10/1988 |
| JP | 2006-204464 A | 8/2006 |
| JP | 2008-522700 A | 7/2008 |
| KR | 20070000421 A | 1/2007 |
| KR | 10-2008-0089802 A | 10/2008 |
| KR | 101036674 B1 | 5/2011 |
| KR | WO 2011/118950 A3 | 9/2011 |

* cited by examiner

*Primary Examiner* — Shay Karls
(74) *Attorney, Agent, or Firm* — Brinks Gilson & Lione (57) ABSTRACT

Disclosed herein is a rotary toothbrush including: a handle installed with a lever; an operating rod operated together with the lever to linearly move in a length direction of the handle; a tilting member coupled to tilting guide grooves of the operating rod to thereby be tilted when the operating rod moves forward; a head part having a shaft rotatably fixed to the tilting member to thereby be tilted together with the tilting member and having bristles implanted therein; a rotation driving member connected to the operating rod and the shaft and rotating the shaft when the operating rod moves forward, thereby allowing the head part to form a T shape with respect to the handle; and a first fixing part provided between the handle and the lever and fixing the lever in a state in which the lever is rotated forward or rearward.

13 Claims, 9 Drawing Sheets

ROTARY TOOTHBRUSH

CROSS-REFERENCE TO RELATED APPLICATION

This application is based on and claims priority from Korean Patent Application Nos. 10-2012-0077935 and 10-2013-0061549, filed on Jul. 17, 2012 and May 30, 2013 in the Korean Intellectual Property Office, the disclosure of which is incorporated herein in its entirety by reference.

BACKGROUND OF THE INVENTION

1. Field of the invention

The present invention relates to a rotary toothbrush, and more particularly, to a rotary toothbrush capable of being freely rotated in a vertical or horizontal direction and capable of stably and accurately performing tooth-brushing by temporarily fixing a head part in which bristles are implanted.

2. Description of the Prior Art

In a generally used toothbrush, a handle and a head part having bristles implanted therein are formed in a linear shape.

However, when teeth are brushed using a linear toothbrush, the tooth-brushing is performed in a horizontal direction, such that foreign materials caught between the teeth are not completely removed and enamel is easily injured, thereby causing a dental disease.

In order to prevent these problems, it has been recommended to brush the teeth from the gums to the ends of the teeth in a scheme similar to combing. However, since it is structurally difficult for the linear toothbrush to move in a vertical direction, the teeth are habitually brushed in the horizontal direction, such that injury to the enamel may not be basically prevented.

Meanwhile, even though the tooth-brushing is performed in the vertical direction using the linear toothbrush, much movement of the wrist joint is generated, such that the wrist joint is easily injured.

Therefore, the present applicant has disclosed 'Rotary Toothbrush' in Korean Patent No. 1036674 so that tooth-brushing may be easily performed in the vertical direction as well as in the horizontal direction.

That is, in the rotary toothbrush according to the related art, a head part in which bristles are implanted is horizontally or vertically rotatable, such that the tooth-brushing may be freely performed in the vertical or horizontal direction.

However, in the rotary toothbrush according to the related art, the head part is horizontally rotated in some degree at the time of performing the tooth-brushing, such that it is impossible to stably and accurately perform the tooth-brushing.

SUMMARY OF THE INVENTION

Accordingly, the present invention has been made to solve the above-mentioned problems occurring in the prior art while advantages achieved by the prior art are maintained intact.

One subject to be achieved by the present invention is to provide a rotary toothbrush capable of stably and accurately performing tooth-brushing by temporarily fixing a head part tilted simultaneously with being rotated with respect to a handle, so as not to be rotated.

According to an exemplary embodiment of the present invention, there is provided a rotary toothbrush including: a handle installed with a lever; an operating rod operated together with the lever to linearly move in a length direction of the handle; a tilting member coupled to tilting guide grooves of the operating rod to thereby be tilted when the operating rod moves forward; a head part having a shaft rotatably fixed to the tilting member to thereby be tilted together with the tilting member and having bristles implanted therein; a rotation driving member connected to the operating rod and the shaft and rotating the shaft when the operating rod moves forward, thereby allowing the head part to form a T shape with respect to the handle; and a first fixing part provided between the handle and the lever and fixing the lever in a state in which the lever is rotated forward or rearward.

The first fixing part may include a first fixing protrusion formed at the lever and a first fixing piece provided with a guide groove installed in an inner wall of the handle and having the first fixing protrusion movably inserted thereinto and fixing grooves formed at both distal ends of the guide groove, respectively, and having the first fixing protrusion inserted thereinto and fixed thereto.

The lever may include a lever shaft installed in the handle, a lever body rotated in a front and rear direction of the handle around the lever shaft, and a pressing piece provided on an outer surface of the lever body and rotating the lever body in the front and rear direction, the lever body may be provided with a buffering hole, and the first fixing protrusion may be formed at the lever body between the buffering hole and the pressing piece.

The pressing piece may be detachably coupled to the lever body.

The operating rod and the head part may include a second fixing part provided therebetween, wherein the second fixing part fixes the operating rod in a state which the operating rod moves forward by the lever.

The second fixing part may include a second fixing protrusion formed at one side of the operating rod and a second fixing piece provided in the head part and having the second fixing protrusion caught thereby and fixed thereto when the operating rod linearly moves forward.

A clip connected to a coupling pin may be fitted into a rear end of the operating rod, and the clip may be connected to the lever to linearly move the operating rod in a front and rear direction together with the lever when the lever moves in the front and rear direction.

The clip and the handle may include a third fixing part provided therebetween, wherein the third fixing part fixes the clip in a state in which the clip linearly moves rearward by the lever.

The third fixing part may include a third fixing protrusion formed at one side of the clip and a third fixing piece provided in the handle and having the third fixing protrusion caught thereby and fixed thereto when the clip linearly moves rearward.

The handle may include a handle body provided with the lever and a handle head provided with the head part, and the handle body may include a handle part, a central part connecting the handle part and the handle head to each other, and a lever mounting part provided in the handle part and the central part and having the lever mounted therein.

The handle head and the operating rod at which the shaft is positioned may be provided with a handle cleaning hole and a rod cleaning hole, respectively.

The handle cleaning hole or the rod cleaning hole may have a diameter larger than that of the shaft.

The handle cleaning hole or the rod cleaning hole may be formed in a circular shape on the same vertical axis line.

The rotation driving member may be made of a metal material or a non-metal material having rigidity.

The rotation driving member may be fixed to the operating rod and the shaft using bolts.

BRIEF DESCRIPTION OF THE DRAWINGS

The above and other objects, features and advantages of the present invention will be more apparent from the following detailed description taken in conjunction with the accompanying drawings, in which:

FIGS. 5A to 5C are enlarged views of the rotary toothbrush assembled according to the exemplary embodiment of the present invention, wherein

DETAILED DESCRIPTION OF THE PREFERRED EMBODIMENTS

A rotary toothbrush according to an exemplary embodiment of the present invention includes first to third fixing parts fixing a head part tilted simultaneously with being rotated with respect to a handle and prevents rotation of the head part by the first to third fixing parts, thereby increasing accuracy of tooth-brushing.

Hereinafter, exemplary embodiments of the present invention will be described in detail with reference to the accompanying drawings so that they can be easily practiced by those skilled in the art to which the present invention pertains. However, the present invention may be implemented in various different forms and is not limited to the embodiments provided in the present description. In the accompanying drawings, portions unrelated to the description will be omitted in order to obviously describe the present invention, and similar reference numerals will be used to describe similar portions throughout the present specification.

Figure 1:
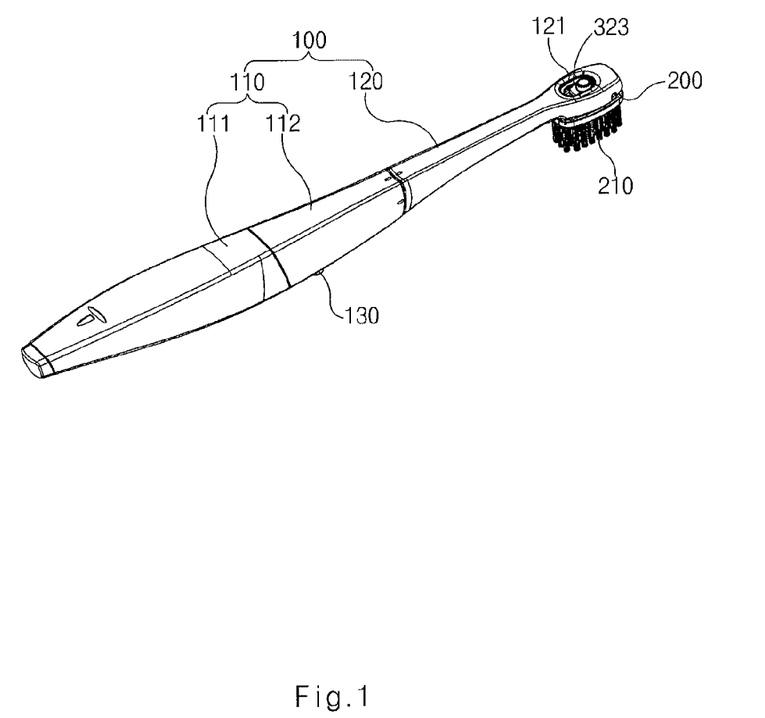
FIG. 1 is an assembled perspective view of a rotary toothbrush according to an exemplary embodiment of the present invention.
Figure 2:
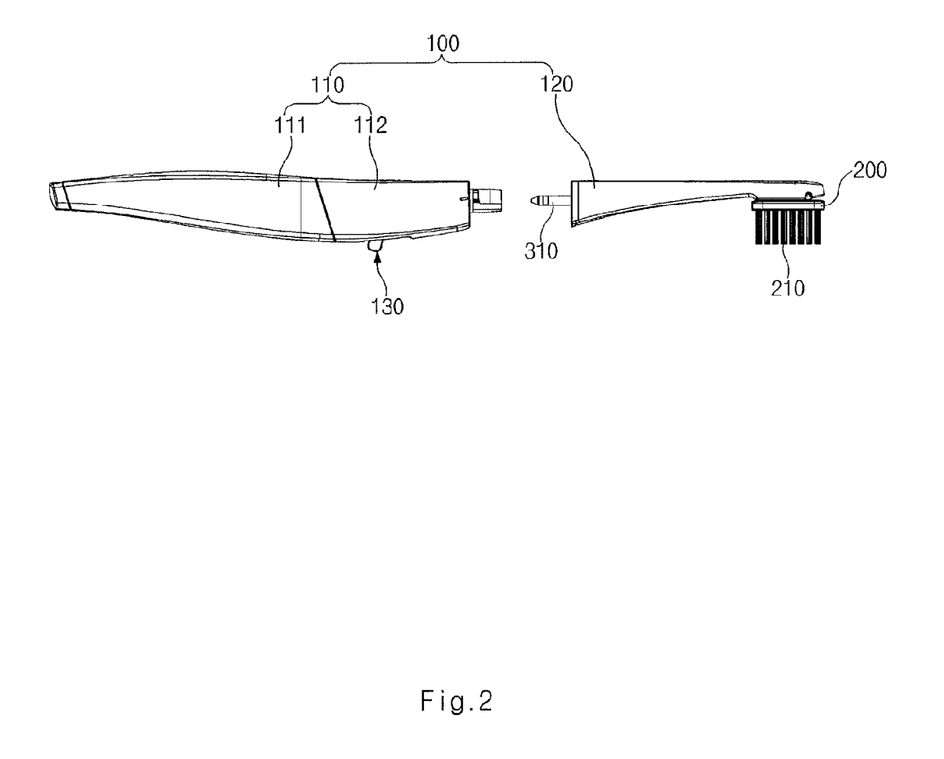
FIG. 2 is a side view of the rotary toothbrush according to the exemplary embodiment of the present invention.
Figure 3:
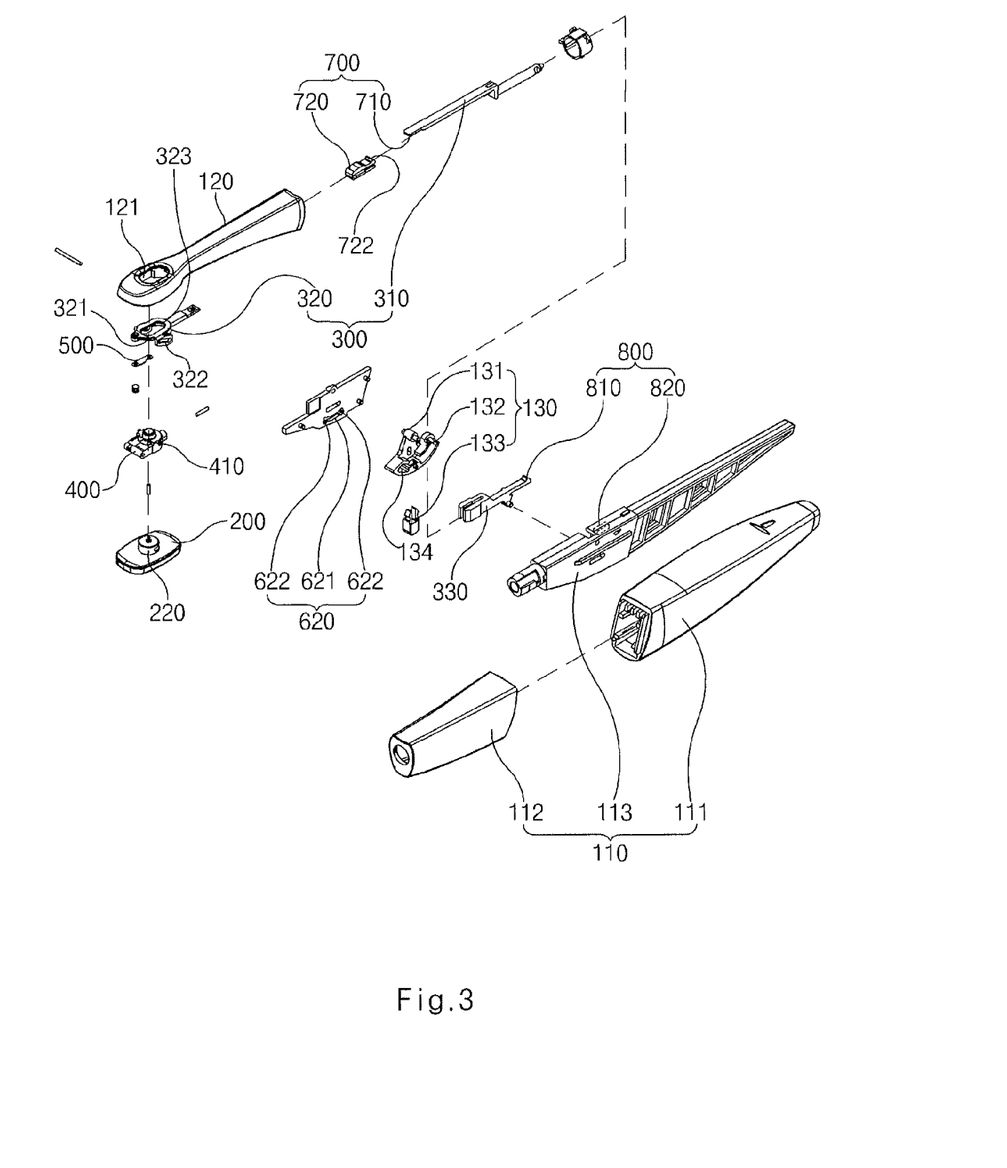
FIG. 3 is an exploded perspective view of the rotary toothbrush according to the exemplary embodiment of the present invention.

The rotary toothbrush according to the exemplary embodiment of the present invention is configured to include a handle 100 installed with a lever 130, a head part 200 having bristles 210 implanted in a lower surface thereof and a shaft 220 provided on an upper surface thereof, an operating rod 300 operated together with the lever 130 to linearly move in a length direction of the handle 100, a tilting member 400 having the shaft 220 rotatably fixed thereto and pressed when the operating rod 300 moves forward to thereby be tilted in an upward direction together with the head part 200, and a rotation driving member 500 connected to the operating rod 300 and the shaft 200 and rotating the shaft 220 when the operating rod 300 moves forward, thereby allowing the head part 200 to form a T shape in a state in which it is tilted with respect to the handle 100, as shown in FIGS. 1 to 3.

In the handle 100, which is to be grasped by a user, a handle body 110 provided with the lever and a handle head 120 provided with the head part are detachably assembled to each other. To this end, an inner side of a rear end of the handle head 120 is provided with a hook protruding toward the handle body 110. The hook is hooked into an inner side of the handle body 110, such that the handle body 110 and the handle head 120 are detachably assembled to each other.

Here, the handle body 110 includes a handle part 111, a central part 112 connecting the handle part 111 and the handle head 120 to each other, and a lever mounting part 113 provided in the handle part 111 and the central part 112 and having the lever 130 mounted therein.

Meanwhile, the central part 112 may be made of any one of a transparent material and a semi-transparent material and have any one or at least two of a red color, a yellow color, a blue color, and a black color.

Meanwhile, the handle body 110, the handle part 111 and the central part 112 having various shapes and sizes may be coupled to both sides of the lever mounting part 113. Therefore, a rotary toothbrush having various shapes and sizes may be implemented.

Meanwhile, the handle body 110 includes the lever 130 installed therein so as to be rotatable in a front and rear direction (a length direction of the rotary toothbrush) around a lever shaft 131.

The lever 130 includes the lever shaft 131 installed in the lever mounting part 113 of the handle body 110, a lever body 132 rotated in a front and rear direction of the handle 100 around the lever shaft 131, and a pressing piece 133 provided on an outer surface of the lever body 132 and rotating the lever body 132 in the front and rear direction.

Here, the pressing piece 133 is coupled to the outer surface of the lever body 132 exposed to the outside of the handle body 110. That is, a coupling part 133a formed in the pressing piece 133 is coupled to a coupling groove 132a formed in the outer surface of the lever body 132. Therefore, in the case in which the pressing piece 133 is worn or damaged due to use, when only the pressing piece 133 is replaced from the lever body 132, the lever 130 may be used.

The handle head 120 has a shape in which it encloses a rod head of an operating rod to be described below.

Figure 4:
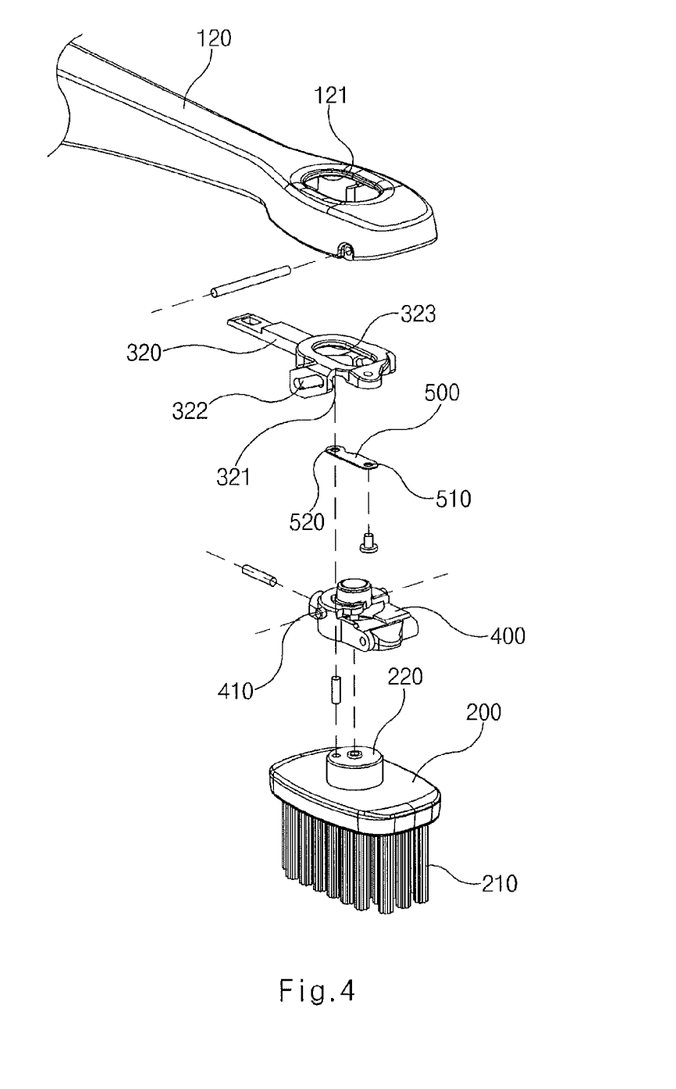
FIG. 4 is an exploded enlarged view of the rotary toothbrush according to the exemplary embodiment of the present invention.
Figure 5A:
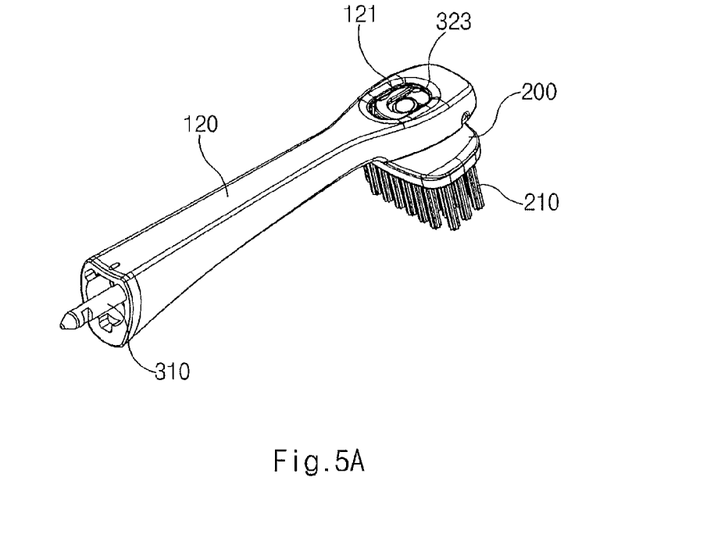
FIG. 5A is a perspective view showing a state in which a handle head is assembled.
Figure 5B:
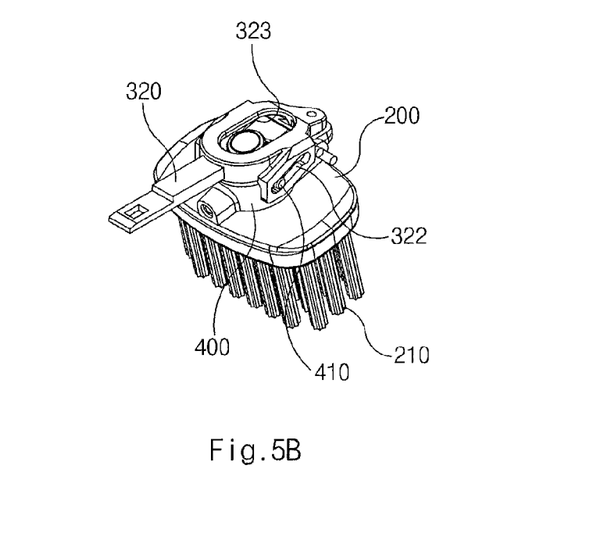
FIG. 5B is a perspective view showing a state in which the handle head is removed.
Figure 5C:
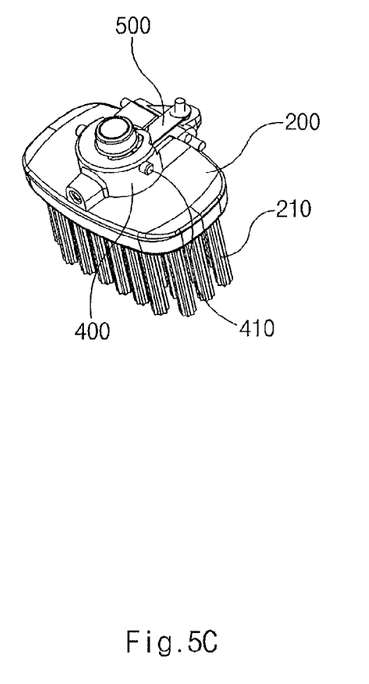
FIG. 5C is a perspective view showing a state in which a rod head is removed.

The head part 200, which is disposed at the handle head 120 to perform tooth-brushing using the implanted bristles 210, has the bristles 210 implanted in the lower surface thereof and the shaft 220 provided on the upper surface thereof, as shown in FIG. 4, wherein the shaft 220 is freely rotatably mounted on the tilting member 400.

The operating rod 300, which is coupled to the lever 130, is provided in the handle 100 and is operated together with the lever 130 to linearly move in the length direction of the handle 100, thereby guiding a tilting member 400 to be described below so as to be tilted by a predetermined angle.

That is, the operating rod 300 includes a rod body 310 connected to the lever 130 so as to be operable together with the lever 130 and a rod head 320 coupled integrally with a front end of the rod body 310 and having tilting guide grooves 322 formed at both sides thereof in order to guide tilting guide protrusions 410 of the tilting member 400, as shown in FIGS. 3 and 5A to 5C.

Meanwhile, a clip 330 connected to a coupling pin is fitted into a rear end of the operating rod 300 and is connected to the lever 130 to linearly move the operating rod 300 together with the lever 130 in the front and rear direction when the lever 130 moves in the front and rear direction.

The rod head 320 includes a guide groove 321 formed in a lower surface thereof so as to penetrate therethrough toward the front of the handle 100 and tilting guide grooves 322 formed in inner walls of both sides of the guide groove 321.

In addition, the tilting guide grooves 322 are formed in the inner walls of the guide groove 321 in the length direction of the handle 100 and are gradually inclined downward from one side toward the other side, such that the head part 200 vertically moves together with the tilting member 400 in the case in which the tilting guide protrusions 410 of the tilting member 400 moves along the tilting guide grooves 322. In this case, the rotation driving member 500 is fixed to the shaft 220 of the head part 200, such that one side of the head part 200 is fixed so as not to move downward and the other side thereof moves downward, thereby tilting the tilting member 400 together with the head part 200 by a predetermined angle.

The tilting member 400 has the shaft 220 of the head part 200 rotatably inserted thereinto and supported thereby, is inserted into the guide groove 321 of the rod head 320, and includes the tilting guide protrusions 410 formed on outer walls of both sides thereof, wherein the tilting guide protrusions 410 are coupled to the tilting guide grooves 322.

That is, the tilting member 400 is pressed when the operating rod 300 moves forward, such that it is tilted by a predetermined angle while the tilting guide protrusions 410 of the tilting member 400 move along the tilting guide grooves 322.

The rotation driving member 500, which is to rotate the head part 200 together with the tilting member 400, has a pin shape and has both end portions each connected and fixed to the operating rod 300 and the shaft 220.

That is, the rotation driving member 500 has one end 510 fixed to the operating rod 300 and the other end 520 freely rotatably fixed to the shaft 220.

Therefore, when the operating rod 300 moves forward, the head part 200 as well as the tilting member 400 receive force for moving them forward. In this case, the head part 200 is rotated simultaneously with moving forward by fixing force of the other end 520 of the rotation driving member 500 and is tilted by a predetermined angle while being pressed downward by pressing force of the other end 520 of the rotation driving member 500.

Therefore, the rotation driving member 500 serves to press the head part 200 so as to be tilted simultaneously with rotating the head part 200. Therefore, the head part 200 forms a T shape in a state in which it is tilted with respect to the handle 100 by a predetermined angle.

Meanwhile, an angle at which the head part 200 is tilted with respect to the handle 100 is 1 to 30 degrees, preferably, 3 to 15 degrees.

Here, the rotation driving member 500 is made of a metal material or a non-metal material so as to minimize interference with the operating rod 300, the shaft 220, and the like, at the time of an operation and minimize a volume of the handle 100 and so as not to be damaged even in the case of being used for a long period of time.

Figure 6:
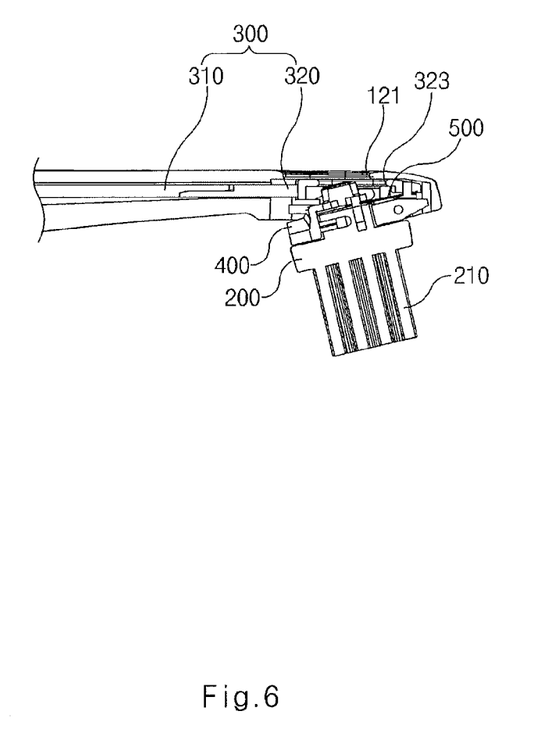
FIG. 6 is a cross-sectional view of the rotary toothbrush according to the exemplary embodiment of the present invention.

Meanwhile, both end portions of the rotation driving member 500 are connected and fixed to the operating rod 300 and the shaft 220 using bolts as shown in FIG. 6. Therefore, both end portions of the rotation driving member 500 are more firmly fixed to press the head part 200 at the time of tilting the head part 200, thereby preventing movement of the head part 200 in the front and rear direction at the time of performing tooth-brushing and preventing injury to the teeth while weakly buffering the head part 200 in the case in which the head part 200 is strongly pressed.

That is, in the case in which the tooth-brushing is performed, the rotation driving member 500 made of the metal material or the non-metal material not only prevents the movement of the head part 200 to induce stable tooth-brushing, but also serves to buffer the head part 200 so as to prevent injury to the teeth in the case in which the tooth-brushing is performed in a state in which the head part 200 is strongly pressed.

In the rotary toothbrush according to the exemplary embodiment of the present invention having the configuration as described above, at the time of operating the lever 130 of the handle 100, the head part 200 is tilted together with the tilting member 400 by a predetermined angle while the operating rod 300 moves forward, and the head part 200 forms a T shape with respect to the handle 100 by the rotation driving member 500.

Therefore, when the tooth-brushing is performed in a state in which the head part 200 forms the T shape with respect to the handle 100, the tooth-brushing may be performed so that the toothbrush is vertical to the teeth, a wrist may be protected, and efficiency of the tooth-brushing may be increased.

Here, the handle 100 and the operating rod 300 include a handle opening hole 121 and a rod opening hole 323 formed at a portion at which the tilting member 400 provided with the shaft 220 is positioned, respectively, as shown in FIGS. 4 and 5.

The handle opening hole 121 and the rod opening hole 323 are formed in the same shape and on the same vertical axis line in the handle 100 and the operating rod 300 at the portion at which the tilting member 400 provided with the shaft 220 is positioned in the case in which the tooth-brushing is performed.

That is, in the case in which foreign materials such as toothpaste, leftovers of food, and the like, are introduced into the handle head 120 including the shaft 220, the operating rod 300, and the tilting member 400, they may be effectively removed using a cotton swab or water pressure through the handle opening hole 121 and the rod opening hole 323.

Meanwhile, the handle opening hole 121 and the rod opening hole 323 have a circular shape. Therefore, the handle opening hole 121 and the rod opening hole 323 are aesthetic and do not have an edge, such that cleaning efficiency is increased.

Meanwhile, in the rotary toothbrush according to the exemplary embodiment of the present invention, the head part 200 in which the bristles 210 are implanted is temporarily fixed in a state in which it is rotated leftward or rightward, such that the head part 200 is not rotated, thereby making it possible to stably and accurately perform tooth-brushing.

Figure 7:
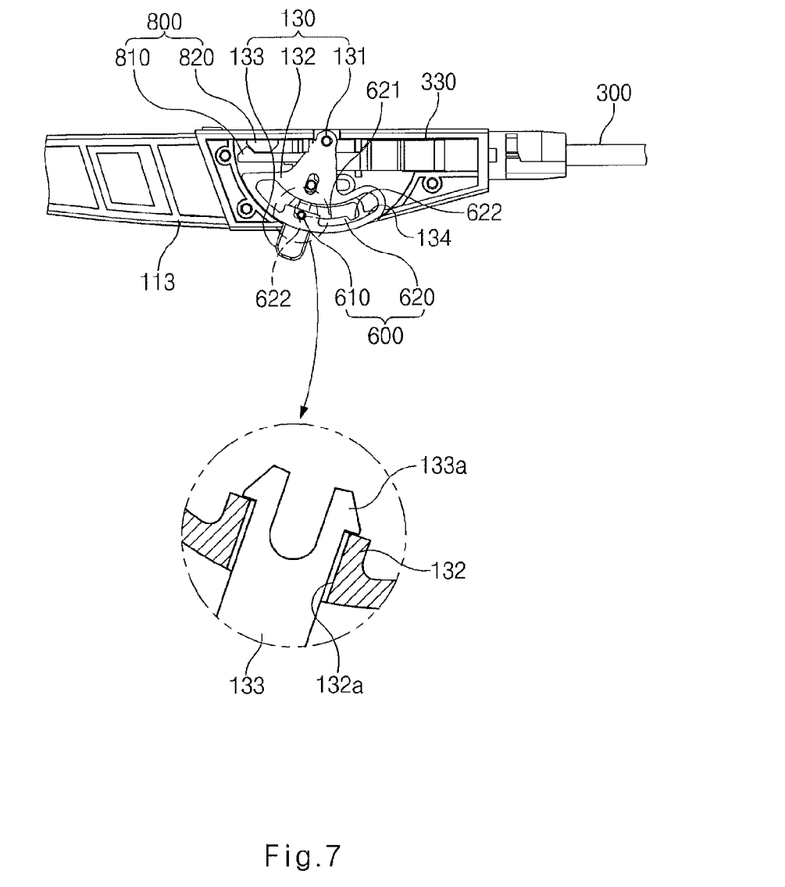
FIG. 7 is a cross-sectional view showing first and third fixing parts of the rotary toothbrush according to the exemplary embodiment of the present invention.

That is, the handle 100 and the lever 130 include a first fixing part 600 provided therebetween so that the lever 130 is rotated forward or rearward and be then inserted and fixed, as shown in FIG. 7, wherein the first fixing part 600 maintains the head part 200 in a T or I shape from the handle 100.

That is, the first fixing part 600 includes a first fixing protrusion 610 formed at the lever 130 and a first fixing piece 620 provided with a guide groove 621 installed in an inner wall of the lever mounting part 113 and having the first fixing protrusion 610 movably inserted thereinto and fixing grooves 622 formed at both distal ends of the guide groove 621, respectively, and having the first fixing protrusion 610 inserted thereinto and fixed thereto.

In the first fixing part 600 as described above, the first fixing protrusion 610 moves forward along the guide groove 621 together with the lever 130 when the lever 130 is rotated toward the front of the handle 100. In this case, the first fixing protrusion 610 is inserted into and fixed to the fixing groove 622 formed at a front distal end of the guide groove 621 to fix the lever 130 so as not to be rotated rearward, thereby fixing the head part 200 in a state in which the head part 200 is rotated forward.

Then, when the lever 130 is strongly rotated rearward, the first fixing protrusion 610 is separated from the fixing groove 622 together with the lever 130, moves along the guide groove 621, and is then inserted into and fixed to the fixing groove 622 formed at a rear distal end of the guide groove 621. Therefore, the head part 200 connected to the lever 130 is fixed in a state in which it is rotated.

Therefore, the first fixing part 600 fixes the lever 130 in a state in which the lever 130 is rotated forward or rearward to fix the head part 200 in a state which the head part 200 is rotated, thereby making it possible to stably and accurately perform tooth-brushing.

Meanwhile, the lever body 132 includes a buffering hole 134 formed in the front and rear direction, and the first fixing protrusion 610 is formed between the buffering hole 134 and the pressing piece 133.

That is, when the pressing piece 133 is pressed, the lever body 132 is compressed by the buffering hole 134, such that the first fixing protrusion 610 moves upward. Therefore, the first fixing protrusion 610 fixed to the fixing groove 622 may be easily separated.

Figure 8:
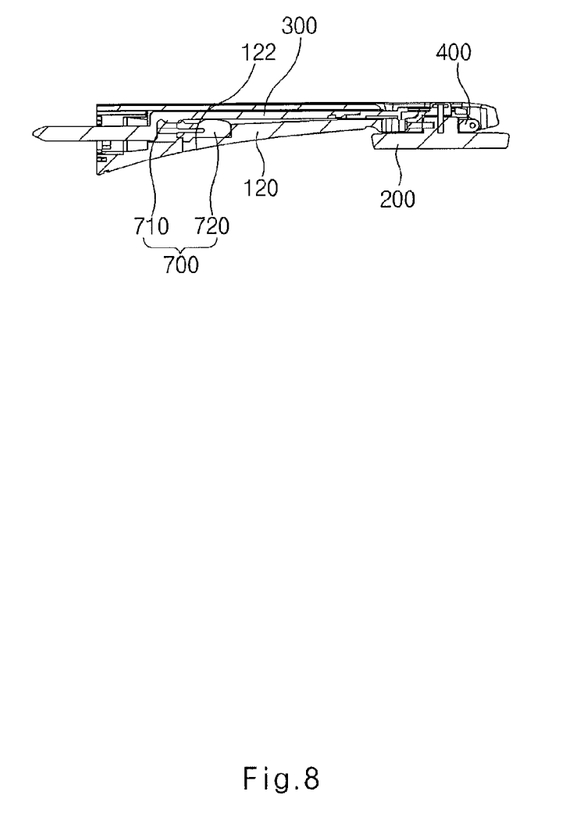
FIG. 8 is a cross-sectional view showing a second fixing part of the rotary toothbrush according to the exemplary embodiment of the present invention.

Meanwhile, the operating rod 300 and the head part 200 include a second fixing part 700 provided therebetween so that the operating rod 300 linearly moves forward by the lever 130 and is then caught and fixed, as shown in FIG. 8, wherein the second fixing part 700 fixes the head part 200 in a state which the head part 200 is rotated in a T shape from the handle 100.

That is, the second fixing part 700 includes a second fixing protrusion 710 formed at one side of the operating rod 300 and a second fixing piece 720 provided in the head part 200 and having the second fixing protrusion 710 caught thereby and fixed thereto when the operating rod 300 linearly moves forward.

Therefore, the second fixing part 700 fixes the head part 200 in a state in which the head part 200 is rotated in the T shape, together with the first fixing part 600.

Meanwhile, the clip 330 and the handle 100 include a third fixing part 800 provided therebetween so that the clip 330 linearly moves rearward by the lever 130 and is then caught and fixed, as shown in FIG. 7, wherein the third fixing part 800 fixes the head part 200 in a state which the head part 200 is rotated in an I shape from the handle 100.

That is, the third fixing part 800 includes a third fixing protrusion 810 formed at one side of the clip 330 and a third fixing piece 820 provided in the handle 100 and having the third fixing protrusion 810 inserted thereinto and fixed thereto when the clip 330 linearly moves rearward.

Therefore, the third fixing part 800 fixes the head part 200 in a state in which the head part 200 is rotated in the I shape, together with the first fixing part 600.

As described above, the head part is temporarily fixed by the first to third fixing parts 600, 700, and 800 so as not to be rotated, thereby making it possible to stably and accurately perform tooth-brushing.

According to the exemplary embodiment of the present invention, the head part is temporarily fixed by the first to third fixing parts so as not to be rotated, thereby making it possible to stably and accurately perform tooth-brushing.

In addition, the handle opening hole and the rod opening hole are formed in the handle head at which the head part is positioned, thereby making it possible to remove foreign materials such as toothpaste and leftovers of food. Therefore, operability and cleanness may be maintained.

It should be interpreted that the scope of the present invention is defined by the following claims rather than the above-mentioned detailed description and all modifications or alterations deduced from the meaning, the scope, and equivalences of the claims are included in the scope of the present invention.

What is claimed is:

1. A rotary toothbrush comprising:
a handle installed with a lever;
an operating rod operated together with the lever to linearly move in a length direction of the handle;
a tilting member coupled to tilting guide grooves of the operating rod to thereby be tilted when the operating rod moves forward;
a head part having a shaft rotatably fixed to the tilting member to thereby be tilted together with the tilting member and having bristles implanted therein;
a rotation driving member connected to the operating rod and the shaft and rotating the shaft when the operating rod moves forward, thereby allowing the head part to form a T shape with respect to the handle; and
a first fixing part provided between the handle and the lever and fixing the lever in a state in which the lever is rotated forward or rearward,
wherein the first fixing part includes a first fixing protrusion formed at the lever and a first fixing piece provided with a guide groove installed in an inner wall of the handle and having the first fixing protrusion movably inserted thereinto and fixing grooves formed at both distal ends of the guide groove, respectively, and having the first fixing protrusion inserted thereinto and fixed thereto.

2. The rotary toothbrush of claim 1, wherein the lever includes a lever shaft installed in the handle, a lever body rotated in a front and rear direction of the handle around the lever shaft, and a pressing piece provided on an outer surface of the lever body and rotating the lever body in the front and rear direction, and
the lever body is provided with a buffering hole, and the first fixing protrusion is formed at the lever body between the buffering hole and the pressing piece.

3. The rotary toothbrush of claim 2, wherein the pressing piece is detachably coupled to the lever body.

4. The rotary toothbrush of claim 1, wherein the operating rod and the head part include a second fixing part provided therebetween, the second fixing part fixing the operating rod in a state which the operating rod moves forward by the lever.

5. The rotary toothbrush of claim 4, wherein the second fixing part includes a second fixing protrusion formed at one side of the operating rod and a second fixing piece provided in the head part and having the second fixing protrusion caught thereby and fixed thereto when the operating rod linearly moves forward.

6. The rotary toothbrush of claim 1, wherein a clip connected to a coupling pin is fitted into a rear end of the operating rod, and
the clip is connected to the lever to linearly move the operating rod in a front and rear direction together with the lever when the lever moves in the front and rear direction.

7. The rotary toothbrush of claim 6, wherein the clip and the handle include a third fixing part provided therebetween, the third fixing part fixing the clip in a state in which the clip linearly moves rearward by the lever.

8. The rotary toothbrush of claim 7, wherein the third fixing part includes a third fixing protrusion formed at one side of the clip and a third fixing piece provided in the handle and having the third fixing protrusion caught thereby and fixed thereto when the clip linearly moves rearward.

9. The rotary toothbrush of claim 1, claim 2 or claim 8, wherein the handle includes a handle body provided with the lever and a handle head provided with the head part, and
the handle body includes a handle part, a central part connecting the handle part and the handle head to each other, and a lever mounting part provided in the handle part and the central part and having the lever mounted therein.

10. The rotary toothbrush of claim 9, wherein the handle head and the operating rod at which the shaft is positioned are provided with a handle cleaning hole and a rod cleaning hole, respectively.

11. The rotary toothbrush of claim 10, wherein the handle cleaning hole or the rod cleaning hole has a diameter larger than that of the shaft.

12. The rotary toothbrush of claim 10, wherein the handle cleaning hole or the rod cleaning hole is formed in a circular shape on the same vertical axis line.

13. The rotary toothbrush of claim 10, wherein the rotation driving member is made of a metal material or a non-metal material having rigidity.

\* \* \* \* \*